United States Patent [19]

Shioyama

[11] Patent Number: 4,479,009

[45] Date of Patent: Oct. 23, 1984

[54] AMINATION PROCESS

[75] Inventor: Tod K. Shioyama, Bartlesville, Okla.

[73] Assignee: Phillips Petroleum Company, Bartlesville, Okla.

[21] Appl. No.: 445,310

[22] Filed: Nov. 29, 1982

[51] Int. Cl.$^3$ ............................................. C07C 85/06
[52] U.S. Cl. ................................................. 564/447
[58] Field of Search ...................................... 564/447

[56] References Cited

U.S. PATENT DOCUMENTS

| | | | |
|---|---|---|---|
| 3,087,966 | 4/1963 | Currier et al. | 564/447 |
| 3,239,562 | 3/1966 | Barker | 564/447 |
| 3,283,002 | 11/1966 | Brake | 260/563 |
| 3,347,926 | 10/1967 | Zech | 564/447 X |
| 3,364,261 | 1/1968 | Van Munster | 564/447 |
| 3,551,485 | 12/1970 | Raff et al. | 260/563 |
| 3,804,901 | 4/1974 | Noeske et al. | 564/447 X |
| 4,014,933 | 3/1977 | Boettger et al. | 260/563 R |
| 4,153,581 | 5/1979 | Habermann | 252/472 |

FOREIGN PATENT DOCUMENTS 1359880  7/1974  United Kingdom ............... 564/447

Primary Examiner—Paul F. Shaver
Attorney, Agent, or Firm—A. W. Umphlett

[57] ABSTRACT

The production of cyclic amines by the amination of cyclic alcohols is made more efficient by carrying out the reaction in the presence of certain amine solvents.

14 Claims, No Drawings

AMINATION PROCESS

BACKGROUND

The diamine 2,2'-bis(4-aminocyclohexyl) propane (PACP) is useful in combination with diacids for the production of polyamides. PACP can be produced by the reaction of ammonia and 2,2'-bis(4-hydroxycyclohexyl) propane (HBPA) in the presence of suitable catalysts. Due to the high melting point of PACP, a solventless workup of the product usually involves the use of temperatures in excess of 160° C.

THE INVENTION

It has been discovered that the catalytic amination to PACP can be carried out more efficiently in the presence of one or more amine solvents. In addition, product workup is facilitated because high temperatures are not required due to the presence of a solvent.

In accordance with the invention, HBPA is converted to PACP in the presence of ammonia and a suitable catalyst with hydrogenation activity, e.g., a nickel- or cobalt-containing catalyst, and an amine solvent, such as cyclohexylamine. Conversions and selectivities are comparable to those attained in the absence of solvent, but workup is greatly simplified.

OBJECTS OF THE INVENTION

It is an object of the invention to provide an improved process for the production of cyclic amines from cyclic alcohols.

It is another object to provide a process in which cycloaliphatic hydroxyl compounds can be aminated effectively in the presence of solvents.

It is yet another object to provide a method by which bis(cyclohexyl) alcohols can be more efficiently aminated and recovered via the use of catalytic reactions in the presence of solvents.

ADVANTAGES

Use of the process described herein has several advantages over art-recognized processes. Since the reaction is not a solventless one, the cyclic amine products need not be handled at high temperatures in order to be recovered for subsequent use. Furthermore, the presence of amine solvents has little or no effect on conversions and selectivities, but greatly facilitates the recovery and processing of the high melting point products.

DESCRIPTION OF THE INVENTION

Solvents

Operable solvents for use in the invention are organic amines whose presence will not be detrimental to either the amination reaction or the subsequent recovery and processing of amine products. Suitable solvents include compounds of the general formula:

RR'NH where R can be hydrogen, a $C_1$ to $C_4$ alkyl group, or a $C_1$ to $C_6$ alkylene bridge, with hydrogen, methyl, ethyl, and methylene substitution preferred; and R' can be a straight chain, branched chain, or cyclic alkyl group containing from 1 to about 16 carbon atoms. Typical solvents include butylamine, pentylamine, hexylamine, octylamine, decylamine, N-methyl-N-butylamine, cyclohexylamine, N-methyl-N-cyclohexylamine, piperidine, 4-methylpiperidine, and the like. Preferred solvents include cyclohexylamine, octylamine, and hexylamine. Mixtures of solvents can be employed.

Reactants

The reactants employed in the process of the invention are cyclic alcohols and suitable amination agents.

Useful alcohols generally contain cycloalkane moieties and conform to the formula $X[YOH]_n$, wherein X is hydrogen, a $C_1$ to $C_6$ organic group or link, or a direct link between Y groups; Y is a cycloaliphatic group; and n is 1 or 2. It is preferred that X be either a direct bond or a straight chain, branched chain, or cyclic alkylene moiety. It is preferred that Y contains 5 or 6 carbon atoms, with 6 highly preferred. Hydrogenated bisphenol A (HBPA), i.e. 2,2'-bis(4-hydroxycyclohexyl) propane, is a preferred reactant.

HBPA of varying purity from a variety of suppliers can be used. The conversion of HBPA and selectivity to PACP depends upon, and is calculated, based upon, the HBPA content of the feed. The purity of several commercially available HBPA feeds is indicated in Table I.

TABLE I

| Supplier | Purity, wt % HBPA |
| --- | --- |
| Rhone-Poulenc | 84.8–96.6 |
| Milliken | 83.8–95.9 |
| Mobay | 90.5 |
| New Japan | 92.8 |

Any amination agent useful for the conversion of similar alcohols to amines may be used herein so long as it is compatible with the reactants and desired products under the conditions used. Suitable amination reagents include ammonia and straight chain primary amines containing up to about 4 carbons. The preferred reagent for amination is ammonia. The use of ammonia to convert cyclic alcohols to cyclic amines is described in U.S. Pat. Nos. 3,283,002 and 3,551,485. The disclosures of those patents are hereby incorporated herein by reference.

The ratio of cyclic alcohol to the amination agent used can vary depending upon reaction conditions, such as the type of reactor and the nature of the reactants employed. Generally, molar ratios of about 1:1 to about 1:100, preferably about 1:5 to about 1:40, will be employed.

The type of reactor employed is not critical. However, the operator should select an apparatus whose features are suited to the particular reactants and the reaction conditions which are generally called for with organic conversions of this type. Both batch and continuous modes can be used. Typical continuous reactor setups can employ downflow, e.g. trickle bed, operation or upflow, e.g. flooded bed, operation. The upflow mode is generally preferred.

Typically the feed will comprise a solution of from about 20 to about 35 weight percent cyclic alcohol in amine solvent. Preferred solutions contain about 20 weight percent cyclic alcohol reactant. It is observed that concentrations above 35 weight percent cause problems with alcohol precipitation and subsequent plugging of the reactor; while concentrations which are too low are not economically attractive because of additional solvent requirements, the additional cost of solvent removal or recycle, and reduced reactor productivity.

Catalyst

A variety of commercially available catalysts can be employed in the invention. While any of the known Group VIII metal catalysts having utility for hydrogenation reactions can be used, it is generally preferred that a catalyst containing at least one of nickel and cobalt be employed in the process of the invention. A brief summary of salient features of some preferred catalysts is given in Table II.

TABLE II

| Catalyst | Active Component (wt %) | Support | Surface area, $m^2/g$ |
| --- | --- | --- | --- |
| Calsicat E235TR | Ni (43) | $Al_2O_3$ | 151 |
| Calsicat E230TR | Ni (57) | $Al_2O_3$ | 148 |
| Calsicat E237TR | Ni (54) | $Al_2O_3$ | 126 |
| Harshaw D-4812 T 1/8" | Co (85) | $Al_2O_3$ | 11.3 |

Reaction Procedures

The following description portrays a typical reaction sequence. The general procedure discussed was employed for laboratory scale fixed bed runs. The reactor was charged with catalyst, then pressure tested. Catalyst was then heated to the desired reaction temperature under a flow of hydrogen. Once reaction temperature was achieved, the reactor was pressured up to reaction pressure. Hydrogen flow was discontinued and pure solvent was introduced. After about 30 minutes, solvent introduction was stopped and pumping of the feed mixture (typically 4:1 wt ratio of cyclohexylamine to HBPA) was started, along with ammonia flow. Ammonia and HBPA-containing feed stream flows were adjusted until desired rates of introduction were obtained. Sampling commenced about 2 hours after feed flow rates were adjusted to desired levels.

Feed flows can be expressed in terms of weight hourly space velocity (WHSV). For HBPA feed, the WHSV is based on the weight of the total solution (only 20 wt% HBPA) which has a density of about 1.2. Suitable WHSV for HBPA feed solution is about 0.1 to about 4.0 with the preferred range of about 0.5 to about 1.2. Suitable ammonia flow rates are determined by the minimum amount required for reaction (and to minimize HBPA decomposition) and the maximum which can be introduced into the reactor without acting as a carrier gas and sweeping unreacted HBPA out of the reactor. Thus, the broad range is about 0.05 to about 3.0 WHSV, and the preferred range is about 0.15 to about 1.0. WHSV of about 0.3 is most preferred.

For reactor shutdown, ammonia and HBPA containing feed introduction was discontinued, and pure solvent (typically cyclohexylamine) or alcohol (such as isobutanol) was pumped over the catalyst bed for about 90 minutes. The heat was then turned off and a small bleed of nitrogen passed over the catalyst before depressurizing to atmospheric pressure.

The laboratory scale continuous reactions were carried out in both downflow (trickle bed) and upflow (flooded bed) operation. A stainless steel tubular reactor was used for both modes of operation. The catalytic reactor was 1 inch internal diameter by 30 inches long.

Pilot plant runs were carried out as continuous reactions employing tubular reactors in the upflow mode. A downflow pre-heater connected to an upflow catalyst reactor, each 3" internal diameter × 12' long, was employed.

For batch mode amination reactions, a stainless steel Parr Rocker apparatus or 300 cc or 500 cc stirred tank reactor from Autoclave Engineers, Inc. was used. The reactor was charged with the appropriate amount of catalyst, HBPA, and solvent (if employed). A weight ratio of about 10:1 feed:catalyst was typically employed. The system was flushed three times with nitrogen and pressure checked during the last nitrogen flush, then flushed three times with hydrogen. The desired amount of anhydrous ammonia was then introduced, and the overall reactor pressure increased by 50 psig with hydrogen. The reactor was heated to the desired reaction temperature with stirring (or rocking). When the desired reaction time had elapsed, the reactor was cooled to about 190°–200° C., stirring stopped and reactor vented. Reaction product was poured from the reactor for analysis.

Samples were analyzed by gas chromatography (GC) on a Hewlett Packard 5710A chromatograph equipped with a flame ionization detector. A 4' × 1/8" column packed with 80/100 mesh Tenax G.C. at 270° C. was employed. Injection port and detector temperatures were set at 300° C., and a helium flow of 25 mL/min employed.

EXAMPLE I

The amination of HBPA was carried out in batch mode following the general procedure described above. Several runs are presented in Table III, all employing Harshaw D-4812 T 1/8" catalyst. The reactions in Table III were carried out for four hours.

TABLE III

| Run No. | Solvent | Feed Ratios, W/W | | | Reaction Parameters | | | Sel. to PACP, % |
| --- | --- | --- | --- | --- | --- | --- | --- | --- |
| | | Solv/ HBPA | $NH_3$/ HBPA | HBPA/ Cat. | Temp. °C. | Max Press.* | HBPA Conv. % | |
| 1 | None | — | 2:1 | 6.25:1 | 275 | 1500 | 100 | 100 |
| 2 | Cyclohexylamine | 2:1 | 2:1 | 6.25:1 | 275 | 2300 | 100 | 100 |
| 3 | Octylamine | 4:1 | 2.2:1 | 12.5:1 | 250 | 3350 | 100 | 100 |
| 4 | Hexylamine | 4:1 | 2.4:1 | 12.5:1 | 250 | 2450 | 100 | 100 |

*Maximum pressure reached during reaction (psig).

The results of these experiments demonstrate that amines are suitable solvents for the amination reaction of HBPA to give PACP. Results comparable to reaction in the absence of solvent are obtained along with the added ease of product handling without need to heat trace sample handling lines due to the use of a compatible solvent.

EXAMPLE II

Several batch reactions were carried out in the Parr Rocker following the general procedure described above. All reactions were carried out for four hours. Several different nickel catalysts were employed. For those runs marked by an asterisk (*), the same catalyst charge from the previous run was employed. Typically, hot catalyst was exposed to air upon recycle as catalyst was removed from hot, liquid PACP by filtration, decantation or the like. Reagents charged and reaction results are summarized in Table IV.

TABLE IV

| Run No. | Catalyst | Feed Ratio, W/W NH₃/HBPA | HBPA/Cat | Reaction Parameters Temp. °C. | Max Press.** | HBPA Conv. % | Sel. to PACP % |
|---|---|---|---|---|---|---|---|
| 1 | E235TR | 2:1 | 3.1:1 | 275 | 1350 | 100 | 100 |
| 2 | E235TR | 1:1 | 4.2:1 | 275 | 2000 | 100 | 100 |
| 3* | E235TR | 1:1 | 4.2:1 | 275 | 2575 | 9.4 | 0 |
| 4* | E235TR | 1:1 | 4.2:1 | 275 | 2300 | 0 | 0 |
| 5 | E230TR | 2:1 | 3.1:1 | 275 | 1400 | 100 | 100 |
| 6 | E230TR | 1:1 | 4.2:1 | 275 | 2100 | 100 | 99.2 |
| 7* | E230TR | 1:1 | 4.2:1 | 260 | 3700 | 9.3 | 100 |
| 8 | E237TR | 2:1 | 3.1:1 | 275 | 1500 | 100 | 100 |
| 9 | E237TR | 1:1 | 4.2:1 | 275 | 2250 | 100 | 100 |
| 10* | E237TR | 1:1 | 4.2:1 | 275 | 3000 | 87.9 | 44.0 |
| 11* | E237TR | 1:1 | 4.2:1 | 275 | 2200 | 72.6 | 24.0 |

*Same catalyst charge recycled from previous run following hot exposure to air.
**Maximum pressure reached during reaction (psig).

These results indicate that reduced, supported nickel catalysts are suitable for amination of HBPA to give PACP, but that exposure of hot catalyst to air should be avoided.

EXAMPLE III

The laboratory trickle bed reactor was charged with 432.0 g of Harshaw D-4812 T ⅛" catalyst. HBPA was fed as a 20 wt% solution in cyclohexylamine. The general procedure described above was employed to study varied reaction temperatures, pressures, reactant feed rates and the like. Reaction parameters and results are presented in Table V.

TABLE V

| Run No. | Reaction Parameters Temp. °C. | Press. psig | Feed Rates mL/hr HBPA | NH₃ | HBPA Conv. % | Sel. to PACP % |
|---|---|---|---|---|---|---|
| 1 | 227 | 1500 | 95.0 | 170 | 100 | 99.1 |
| 2 | 225 | 1000 | 95.0 | 170 | 100 | 85.1 |
| 3 | 225 | 1000 | 95.0 | 148 | 100 | 95.1 |
| 4 | 226 | 1500 | 157.0 | 148 | 100 | 100 |
| 5 | 227 | 900 | 150.0 | 100 | 100 | 98.8 |
| 6 | 227 | 900 | 153.0 | 100 | 100 | 95.2 |
| 7 | 200 | 900 | 153.0 | 100 | 72.7 | 55.2 |

The results presented in Table V demonstrate that HBPA can be converted to PACP in a continuous manner employing a trickle bed reactor. Excellent results (100% conversion, >95% selectivity) are obtained under a variety of reaction conditions. Reaction temperature of about 225° C. is preferred, with pressure as low as 900 psig giving suitable results.

EXAMPLE IV

A new charge of Harshaw D-4812 T ⅛" catalyst (462.6 g) was placed in the laboratory trickle bed reactor. The general procedure described above was employed to study catalyst lifetime over an extended period of time and a variety of reaction conditions. Reaction parameters employed and results are presented in Table VI.

TABLE VI

| Run No. | Reaction Parameters Time, Hrs. | Temp. °C. | Press. psig | Feed Rates, mL/hr HBPA | NH₃ | HBPA Conv. % | Sel. to PACP % |
|---|---|---|---|---|---|---|---|
| 1 | 9 | 231 | 1515 | 180 | 100 | 100 | 92.0 |
| 2 | 21 | 230 | 1550 | 200 | 100 | 100 | 92.7 |
| 3 | 30 | 225 | 1530 | 205 | 100 | 100 | 95.3 |
| 4 | 40 | 230 | 1505 | 180 | 100 | 100 | 96.8 |
| 5 | 50 | 225 | 1500 | 200 | 100 | 100 | 100 |
| 6 | 60 | 225 | 1495 | 200 | 100 | 100 | 100 |
| 7 | 70 | 225 | 1540 | 200 | 100 | 100 | 100 |
| 8 | 80 | 227 | 1535 | 210 | 100 | 100 | 98.9 |
| 9 | 90 | 225 | 1530 | 210 | 100 | 100 | 100 |
| 10 | 96 | 227 | 1510 | 440 | 180 | 100 | 100 |
| 11 | 100 | 230 | 1510 | 440 | 180 | 100 | 100 |

The results in Table VI demonstrate the operability of Harshaw D-4812 T ⅛" catalyst for the conversion of HBPA to PACP in a trickle bed reactor. Excellent results are obtained over at least 100 hours on stream.

EXAMPLE V

The laboratory trickle bed reactor was charged with 203.1 g of Calsicat E230TR catalyst. HBPA was fed as a 20 wt% solution in cyclohexylamine. The general procedure described above was employed to study catalyst performances over several hours. Reaction parameters and results are presented in Table VII.

TABLE VII

| Reaction Parameters Time Hrs. | Temp. °C. | Press. psig | Feed Rates mL/hr HBPA | NH₃ | HBPA Conv. % | Sel. to PACP % |
|---|---|---|---|---|---|---|
| 1 | 222 | 1485 | 120.0 | 100 | 100 | 49.9 |
| 2 | 223 | 1445 | 120.0 | 100 | 100 | 56.6 |
| 3 | 230 | 1495 | 136.5 | 100 | 100 | 74.2 |
| 4 | 227 | 1480 | 136.5 | 100 | 100 | 90.6 |
| 5 | 224 | 1485 | 136.5 | 100 | 100 | 92.3 |
| 6 | 223 | 1395 | 136.5 | 100 | 99.8 | 82.3 |
| 7 | 226 | 1400 | 136.5 | 100 | 100 | 79.9 |

The results in Table VII demonstrate that Calsicat E230TR is a suitable catalyst for the conversion of HBPA to PACP in a trickle bed reactor.

EXAMPLE VI

The laboratory trickle bed reactor was charged with 181.0 g of Calsicat E235TR catalyst. HBPA was fed as a 20 wt% solution in cyclohexylamine. The general procedure described above was employed to study catalyst performance over several hours, the entire study taking several days to complete. Catalyst bed was flushed with isobutanol according to the general procedure described above prior to cool-down each day. Reactor was then brought back up to temperature under isobutanol flow; then, when reaction conditions had been established, HBPA/NH3 feeds commenced. Reaction parameters and results are presented in Table VIII.

TABLE VIII

| Run No. | Reaction Parameters | | | Feed Rates mL/hr | | HBPA Conv. % | Sel. to PACP % |
|---|---|---|---|---|---|---|---|
| | Time, Hrs. | Temp. °C. | Press. psig | HBPA | NH3 | | |
| 1 | 1 | 219 | 1505 | 120 | 100 | 100 | 100 |
| 2 | 5 | 228 | 1480 | 120 | 100 | 99.1 | 100 |
| 3 | 10 | 222 | 1530 | 125 | 100 | 99.8 | 87.1 |
| 4 | 11 | 232 | 1525 | 125 | 100 | 99.8 | 70.9 |
| 5 | 12 | 236 | 1505 | 125 | 64 | 99.6 | 68.3 |
| 6 | 13 | 242 | 1495 | 125 | 50 | 99.7 | 60.9 |
| 7 | 14 | 254 | 1485 | 125 | 38 | 99.6 | 47.4 |
| 8 | 15 | 235 | 1475 | 125 | 50 | 99.3 | 62.8 |
| 9 | 18 | 223 | 1540 | 125 | 100 | 99.8 | 64.8 |

The results presented in Table VIII demonstrate that Calsicat E235TR is a suitable catalyst for the conversion of HBPA to PACP in a trickle bed reactor.

EXAMPLE VII

The laboratory trickle bed reactor was charged with 185.2 g of Calsicat E237TR catalyst. HBPA was fed as a 20 wt% solution in cyclohexylamine. The general procedure described above was employed to study catalyst performance over several hours, the entire study taking several days. Catalyst bed was treated as described in Example VI for shutdown and start-up during the study. Reaction parameters and results are presented in Table IX.

TABLE IX

| Run No. | Reaction Parameters | | | Feed Rates mL/hr | | HBPA Conv. % | Sel. to PACP, % |
|---|---|---|---|---|---|---|---|
| | Time, hrs. | Temp., °C. | Press. psig | HBPA | NH3 | | |
| 1 | 1 | 214 | 1540 | 150 | 100 | 100 | 97.6 |
| 2 | 3 | 218 | 1530 | 150 | 100 | 100 | 98.3 |
| 3 | 5 | 214 | 1485 | 150 | 100 | 99.8 | 100 |
| 4 | 8 | 223 | 1510 | 160 | 64 | 100 | 98.2 |
| 5 | 10 | 225 | 1525 | 160 | 52 | 100 | 98.8 |
| 6 | 12 | 219 | 1525 | 160 | 45 | 100 | 100 |
| 7 | 15 | 234 | 1510 | 205 | 100 | 100 | 100 |
| 8 | 17 | 239 | 1510 | 205 | 100 | 100 | 99.7 |
| 9 | 20 | 242 | 1520 | 214 | 100 | 100 | 98.7 |
| 10 | 21 | 243 | 1480 | 214 | 100 | 100 | 89.7 |
| 11 | 22 | 264 | 1485 | 214 | 100 | 100 | 79.2 |
| 12 | 23 | 260 | 1440 | 214 | 64 | 100 | 79.4 |
| 13 | 24 | 263 | 1515 | 214 | 50 | 100 | 90.8 |
| 14 | 25 | 265 | 1495 | 214 | 40 | 100 | 86.9 |

The results presented in Table IX demonstrate that Calsicat E237TR is a suitable catalyst for the conversion of HBPA to PACP in a trickle bed reactor. The catalyst is active under a variety of reaction conditions and shows good activity through at least 25 hours on stream.

EXAMPLE VIII

Harshaw D-4812 T ⅛" catalyst (339.1 g) used for lifetime studies described in Example IV was placed in the laboratory upflow reactor and treated with HBPA(20 wt% solution in cyclohexylamine) and ammonia according to the general procedure set forth above. Reaction parameters and results are presented in Table X.

TABLE X

| Run No. | Reaction Parameters | | | Feed Rates, mL/hr | | HBPA Conv. % | Sel. to PACP % |
|---|---|---|---|---|---|---|---|
| | Time, hrs | Temp., °C. | Press. psig | HBPA | NH3 | | |
| 1 | 1 | 242 | 1500 | 93 | 75 | 100 | 49.2 |
| 2 | 17 | 226 | 1500 | 126 | 75 | 100 | 70.4 |
| 3 | 49 | 219 | 1500 | 203 | 75 | 98.3 | 71.3 |
| 4 | 56 | 219 | 1500 | 190 | 75 | 99.9 | 85.2 |
| 5 | 77 | 227 | 1500 | 152 | 50 | 100 | 95.3 |
| 6 | 107 | 229 | 1500 | 179 | 70 | 100 | 91.8 |
| 7 | 131 | 234 | 1500 | 184 | 60 | 99.1 | 96.2 |
| 8 | 141 | 233 | 1500 | 280 | 80 | 100 | 94.3 |
| 9 | 150 | 233 | 1500 | 342 | 90 | 100 | 93.2 |
| 10 | 158 | 240 | 1500 | 360 | 90 | 99.9 | 92.0 |
| 11 | 182 | 233 | 1500 | 245 | 80 | 98.2 | 93.2 |

The results presented in Table X demonstrate that HBPA can be converted to PACP in a continuous reactor operated in the upflow mode employing Harshaw D-4812 T ⅛" catalyst. Catalyst lifetime is shown to be excellent, with excellent conversion and selectivities for over 200 hours reaction.

EXAMPLE IX

The pilot plant reactor was charged with 86 pounds of Harshaw D-4812 T ⅛" catalyst. Reaction was carried out at 225° C. and 1500 psig according to the general procedure set forth above. HBPA (20 wt% in cyclohexylamine) feed rate ranged from 8–9.5 gal/hr. (WHSV 0.65–0.8). Ammonia:HBPA molar ratio of 20:1 was maintained throughout the reaction. About 2000 pounds of HBPA were thereby converted in about 170 hours total reaction time. Complete conversion of HBPA was obtained under all conditions employed.

The results of these experiments demonstrate that the amination of HBPA to give PACP can be successfully carried out on a large scale with good results under conditions comparable to those employed for laboratory studies.

Reasonable variations, such as would occur to one of ordinary skill in the art, may be made herein without departing from the scope of the invention.

I claim:

1. A process for the conversion of cyclic alcohols to cyclic amines comprising contacting one or more cyclic alcohols with an amination agent and a catalyst in the presence of one or more solvents of the general formula:

RR'NH where R is hydrogen, a $C_1$ to $C_4$ alkyl group, or a $C_1$ to $C_6$ alkylene bridge, and R' is an alkyl group having from 1 to about 16 carbon atoms.

2. The process of claim 1 wherein the cyclic alcohol conforms to the general formula:

X[YOH]$_n$ where X is hydrogen, a $C_1$ to $C_6$ organic link or a direct link to adjacent rings, Y is a cycloaliphatic group, and n is 1 or 2.

3. The process of claim 2 wherein the catalyst contains at least one Group VIII metal.

4. The process of claim 2 wherein the catalyst contains at least one of nickel or cobalt.

5. The process of claim 4 wherein the alcohol is hydrogenated bisphenol A and the amination agent is ammonia.

6. The process of claim 5 wherein the solvent is selected from the group consisting of cyclohexylamine, octylamine, hexylamine and mixtures thereof.

7. The process of claim 4 wherein the molar ratio of cyclic alcohol to amination agent is from about 1:1 to about 1:100.

8. The process of claim 6 wherein the molar ratio of cyclic alcohol to amination agent is from about 1:1 to about 1:100.

9. The process of claim 8 wherein the cyclic alcohol is present in a solution containing from about 20 to about 35 weight percent cyclic alcohol in amine solvent.

10. The process of claim 9 in which a trickle bed reactor is employed.

11. The process of claim 9 in which an upflow reactor is employed.

12. The process of claim 5 wherein a 20 weight percent solution of cyclic alcohol is employed as the feed.

13. The process of claim 12 wherein the feed flows through the reactor at a weight hourly spore velocity of about 0.1 to about 4.0.

14. The process of claim 13 wherein the amination agent is supplied to the reactor at a weight hourly space velocity of about 0.05 to about 3.0.

* * * * *